US010066981B2

(12) United States Patent
Hudson

(10) Patent No.: US 10,066,981 B2
(45) Date of Patent: Sep. 4, 2018

(54) DETECTION OF MALFUNCTION OF FLOW MONITORING SYSTEM OF FLOW CONTROL APPARATUS

(71) Applicant: KPR U.S., LLC, Mansfield, MA (US)

(72) Inventor: Joseph A. Hudson, O'Fallon, MO (US)

(73) Assignee: KPR U.S., LLC, Mansfield, MA (US)

( * ) Notice: Subject to any disclaimer, the term of this patent is extended or adjusted under 35 U.S.C. 154(b) by 94 days.

(21) Appl. No.: 15/141,913

(22) Filed: Apr. 29, 2016

(65) Prior Publication Data

US 2016/0320228 A1 Nov. 3, 2016

Related U.S. Application Data

(60) Provisional application No. 62/154,362, filed on Apr. 29, 2015.

(51) Int. Cl.
*A61M 5/168* (2006.01)
*A61M 5/142* (2006.01)
(Continued)

(52) U.S. Cl.
CPC ...... *G01F 25/0007* (2013.01); *A61J 15/0076* (2015.05); *A61M 5/16804* (2013.01);
(Continued)

(58) Field of Classification Search
CPC ............ A61J 15/0076; A61M 5/16804; A61M 5/16831; A61M 2205/3306; G01F 1/66; G01F 25/0007; G06F 19/3468
See application file for complete search history.

(56) References Cited

U.S. PATENT DOCUMENTS 4,474,206 A * 10/1984 Cannon ............... A61M 5/1689
137/486
4,665,391 A * 5/1987 Spani .................. G01F 23/2921
250/577
(Continued)

FOREIGN PATENT DOCUMENTS

EP 0416911 A2 3/1991
EP 2241344 A1 10/2010

OTHER PUBLICATIONS

International Search Report dated Jul. 25, 2016 in related International Application No. PCT/US2016/029925, 6 pages.
(Continued)

*Primary Examiner* — David A Rogers
(74) *Attorney, Agent, or Firm* — Adnan H. Bohri

(57) ABSTRACT

Detection of fluid conditions in a section of tube of an administration set. A light source is positioned adjacent to the tube to transmit an infrared light through the tube and any fluid therein. A light sensor senses the infrared light transmitted through the tube and generates an output signal. A frequency of the output signal is a function of an intensity of the light transmitted through the tube. A processor receives and determines the frequency of the output signal, and compares the determined frequency to threshold frequency values to determine whether fluid is in the tube. The processor also monitors the generated output signal to determine if the frequency of the output signal changes over a predetermined period of time, and determines whether fluid is flowing in the tube as a function of the determined change in frequency.

20 Claims, 9 Drawing Sheets

(51) Int. Cl.
  *G01F 25/00* (2006.01)
  *G06F 19/00* (2018.01)
  *G01F 1/66* (2006.01)
  *A61J 15/00* (2006.01)

(52) U.S. Cl.
  CPC .......... *A61M 5/16831* (2013.01); *G01F 1/66* (2013.01); *G06F 19/3468* (2013.01); *A61M 2205/3306* (2013.01)

(56) References Cited

U.S. PATENT DOCUMENTS

| | | | | |
|---|---|---|---|---|
| 4,865,581 | A * | 9/1989 | Lundquist | A61M 1/1072 600/17 |
| 4,909,797 | A * | 3/1990 | Timothy | A61M 5/1689 128/DIG. 13 |
| 5,256,155 | A * | 10/1993 | Yerlikaya | A61M 5/1689 128/DIG. 13 |
| 5,357,113 | A * | 10/1994 | Liston | G01N 21/37 250/343 |
| 5,798,699 | A * | 8/1998 | Bryant | G01N 21/534 250/338.1 |
| 5,903,006 | A * | 5/1999 | Kiuchi | G01N 21/3577 250/339.12 |
| 6,683,679 | B2 * | 1/2004 | Belenkii | H04B 1/52 356/28 |
| 7,032,461 | B2 * | 4/2006 | Ueki | G01F 1/32 73/861.22 |
| 7,684,938 | B1 | 3/2010 | Feller | |
| 8,373,421 | B2 * | 2/2013 | Lindegger | A61M 5/14244 324/511 |
| 8,795,225 | B2 * | 8/2014 | Lewis | A61M 5/14232 604/122 |
| 2002/0036276 | A1 * | 3/2002 | Seeman | G01N 21/85 250/573 |
| 2004/0121494 | A1 * | 6/2004 | Arno | G01J 5/0014 438/7 |
| 2005/0267418 | A1 * | 12/2005 | Fournie | A61J 15/00 604/249 |
| 2010/0082011 | A1 | 4/2010 | Lewis et al. | |
| 2014/0358081 | A1 | 12/2014 | Dumas, III et al. | |
| 2016/0320228 | A1 * | 11/2016 | Hudson | G01F 1/66 |
| 2017/0216516 | A1 * | 8/2017 | Dale | A61M 39/24 |

OTHER PUBLICATIONS

Written Opinion of the International Searching Authority dated Jul. 25, 2016 in related International Application No. PCT/US2016/029925, 8 pages.

* cited by examiner

DETECTION OF MALFUNCTION OF FLOW MONITORING SYSTEM OF FLOW CONTROL APPARATUS

CROSS-REFERENCE TO RELATED APPLICATION

This application claims the benefit of U.S. Provisional Application No. 62/154,362, filed Apr. 29, 2015.

TECHNICAL FIELD

This invention relates generally to the field of fluid administration to patients via a flow control apparatus, and more particularly, to detection of a malfunction of a flow monitoring system of the flow control apparatus.

BACKGROUND

Administering fluids containing medicine or nutrition to a patient is generally well known in the art. Typically, fluid is delivered to the patient by an administration feeding set loaded to a flow control apparatus, such as a pump, which delivers fluid to a patient.

A flow control apparatus of the prior art may also be capable of monitoring and detecting fluid flow conditions that can occur within the loaded feeding set during operation of the flow control apparatus. For example, prior art flow monitoring systems may include an ultrasonic sensor capable of detecting when fluid is not present in tube of the feeding set. In this example, the ultrasonic sensor transmits an ultrasonic signal through the tube and detects the ultrasonic signal after passing through the tube. The transmitted signal is analyzed, such as by a processor of the flow monitoring system, to determine the presence or absence of fluid within the tube and/or the flow condition of the fluid within the tube. If, for example, the flow monitoring system determines that there is no fluid present in the tube, the flow monitoring system may activate an alarm and/or stop operation of the flow control apparatus to ensure that air is not delivered to the patient.

It is possible that the flow monitoring system may malfunction, whereby the flow monitoring system fails to detect when there is no fluid in the feeding set. For example, the sensor (e.g., the ultrasonic sensor) may malfunction, whereby the sensor detects an ultrasonic signal that is indicative of the presence of fluid within the tube, for example, when in fact no fluid is present in the tube. In such a case, the flow monitoring system would make an incorrect determination that fluid is present in the tube and the flow control apparatus would continue to deliver air to the patient.

BRIEF DESCRIPTION OF THE DRAWINGS

Corresponding reference characters indicate corresponding parts throughout the drawings.

DETAILED DESCRIPTION

Figure 1:
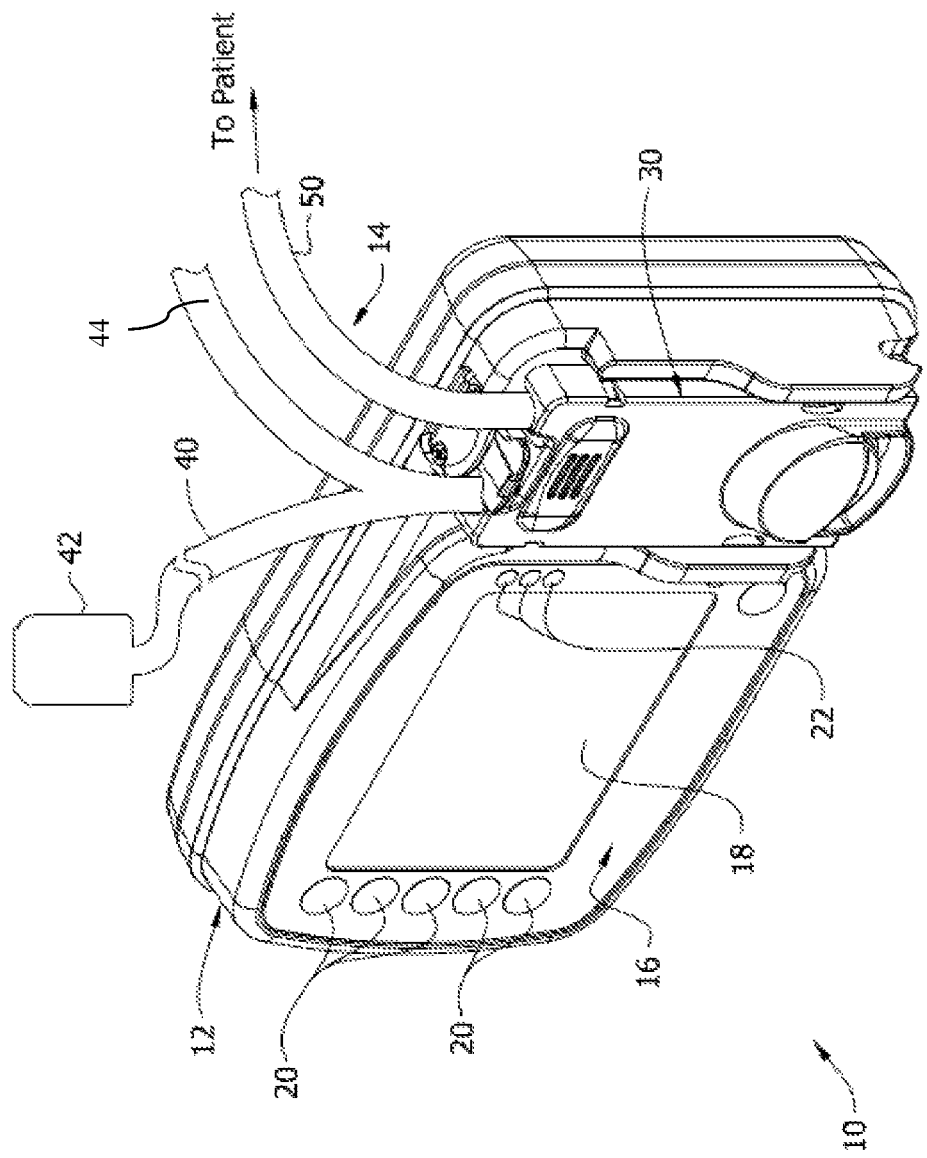
FIG. 1 is a perspective of an enteral feeding pump and a fragmentary portion of a feeding set (illustrated schematically) received on the pump.

Referring now to the drawings, an enteral feeding pump (broadly, "flow control apparatus") constructed according to the principles of the present invention is generally indicated at 10. The feeding pump 10 may comprise a housing, generally indicated at 12, that may be constructed to receive an administration feeding set (broadly, "a fluid delivery set"), generally indicated at 14. It will be understood that although the illustrated flow control apparatus is an enteral feeding pump 10, the present disclosure has application to other types of flow control apparatus (not shown), including medical infusion pumps. Moreover, although an administration feeding set 14 is shown, other types of fluid delivery sets (not shown) can be used within the scope of the present invention.

A user interface, generally indicated at 16, may be provided on the front of the housing 12. The user interface 16 may include a display screen 18 that is capable of displaying information about the status and operation of the pump, a plurality of push buttons 20 on one side of the display screen, and a plurality of LEDs 22 on the other side of the display screen.

Figure 2:
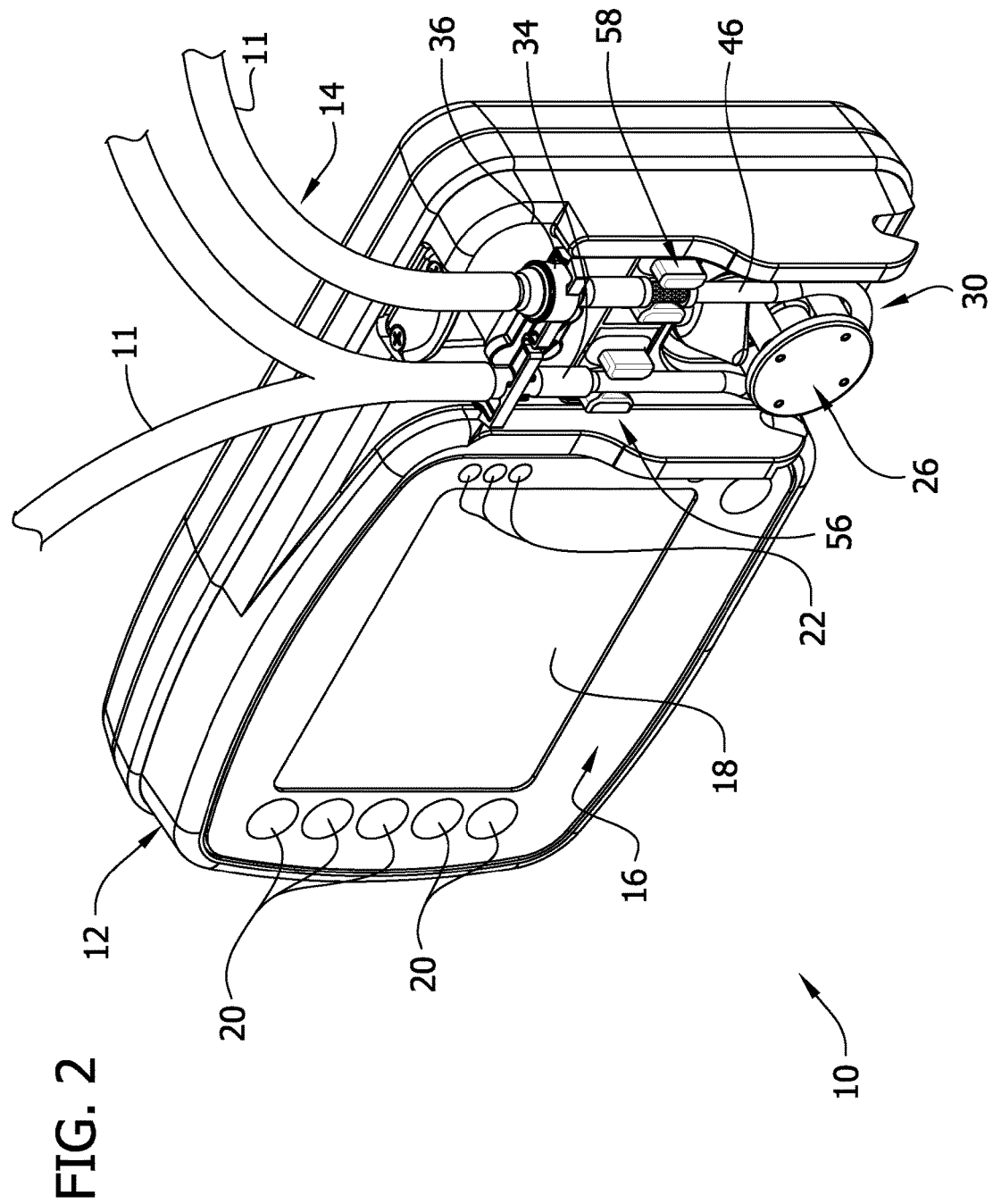
FIG. 2 is a perspective of FIG. 1 with a cassette housing of the feeding set removed.

Referring now to FIGS. 1 and 2, the pump 10 may further comprise a rotor 26 that controls the flow of fluid through the feeding set 14 when a cassette, generally indicated at 30, of the feeding set is loaded on the pump. The cassette 30 may include a valve mechanism 34 and a mounting collar 36 that are releasably securable to the pump 10. The feeding set 14 may include tubing 11 having a first section of tube 40 (e.g., feeding inlet tube) upstream of the valve mechanism 34 leading to a feeding fluid source 42, and a second section of tube 44 (e.g., flushing inlet tube) upstream of the valve mechanism leading to a flushing fluid source (not shown). The feeding set 14, more specifically the cassette 30, may include a third section of tube 46 (e.g., cassette tube) extending between and interconnecting the valve mechanism 34 and the mounting collar 36. A fourth section of tube 50 (e.g., outlet tube) may extend from the mounting collar 36 toward the patient. The valve mechanism 36 may be operable to selectively permit flow of fluid from the feeding fluid source 42 or a flushing fluid source (not shown) into the cassette tube 46, or prevent any fluid flow communication from the feeding or flushing fluid sources into the cassette tube. When loaded onto the pump 10, the valve mechanism 34 and the mounting collar 36 may be securely engaged with the pump, and the cassette tube 46 may be placed in a stretched condition around the rotor 26 of the pump. Rotation of the rotor 26, such as by a motor 52 (FIG. 4), compresses the cassette tube 46 and provides a force for driving fluid in the feeding set 30 from the upstream side of the rotor to the downstream side of the rotor for delivery to the patient.

Referring to FIGS. 1 and 2, at least one fluid sensor associated with the housing 3 may be located in a position to detect a condition of fluid in the feeding set 14. In the illustrated embodiment, the pump 10 includes two fluid sensors: a first fluid sensor, generally indicated at 56, is located upstream of the rotor 26; and a second fluid detector, generally indicated at 58, is located downstream of the rotor. It is understood that the pump 10 may include a single fluid sensor or more than two fluid sensors without departing from the scope of the present invention. In one example, the first and second fluid sensors 56 may be ultrasonic sensors for use in detecting a condition of the fluid in the feeding set 14, although other types of sensors are within the scope of the present invention, including, but not limited to, infrared sensors. The first fluid sensor may be used to detect the presence or absence of fluid in the cassette tube 30, and the second fluid sensor 58 may be used to detect a downstream occlusion. It is understood that the first and second fluid sensors 56, 58 may be configured for use in detecting other conditions of the feeding set 14, such as fluid flow and opaqueness of the fluid.

Figure 4:
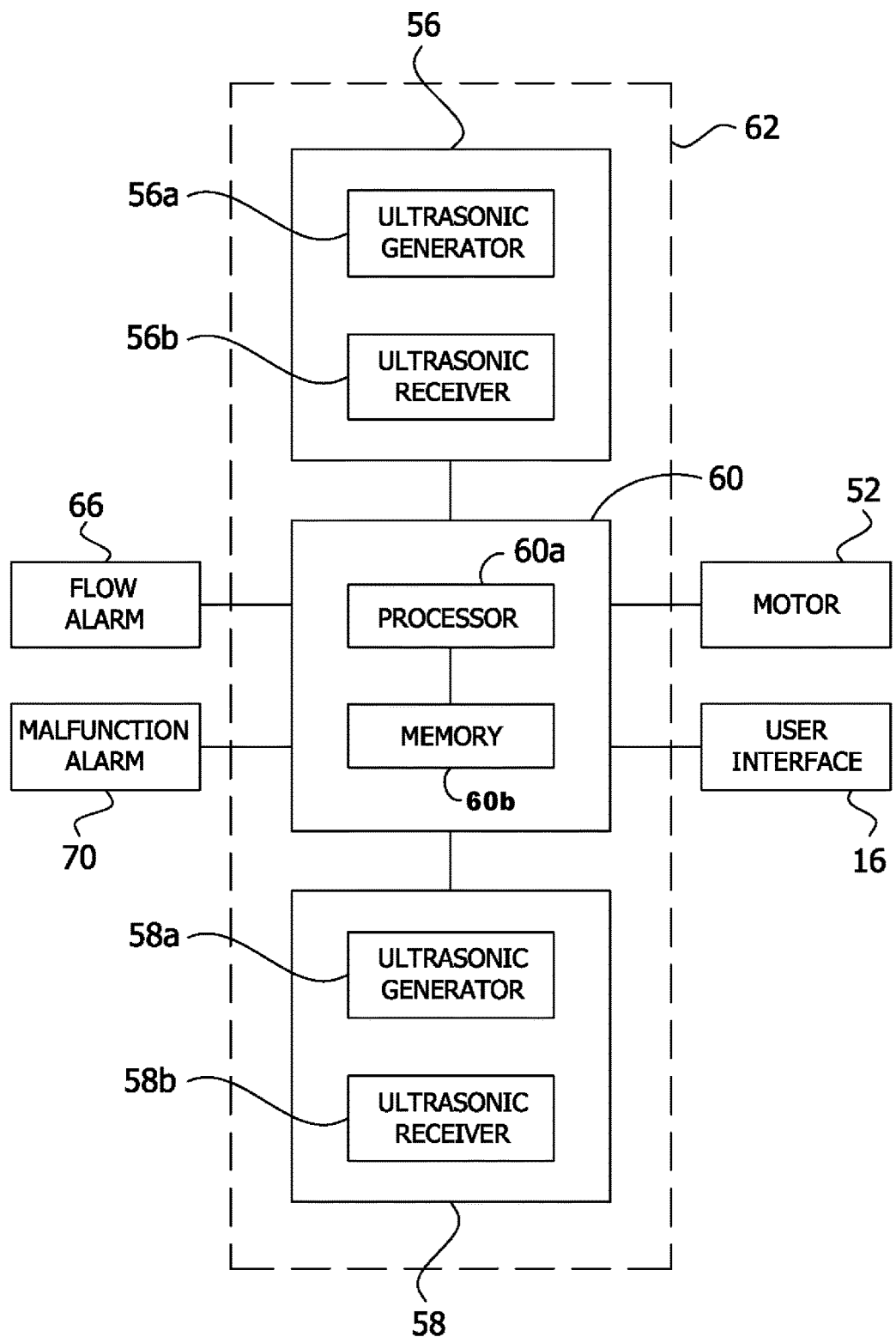
FIG. 4 is an exemplary block diagram illustrating a control unit of the enteral feeding pump and components that are in communication with the control unit.

Referring now to FIG. 4, an exemplary block diagram illustrates a control unit 60 of the enteral feeding pump 10 and components that are in communication with the control unit. The control unit 60 may include a processor 60a (e.g., a microprocessor) and a memory 60b. It is understood that the control unit 60 may comprise more than one controller, each of which may have at least one processor and at least one memory. As illustrated, the control unit 60 is in communication with the motor 52 and the user interface 16.

Figure 3:
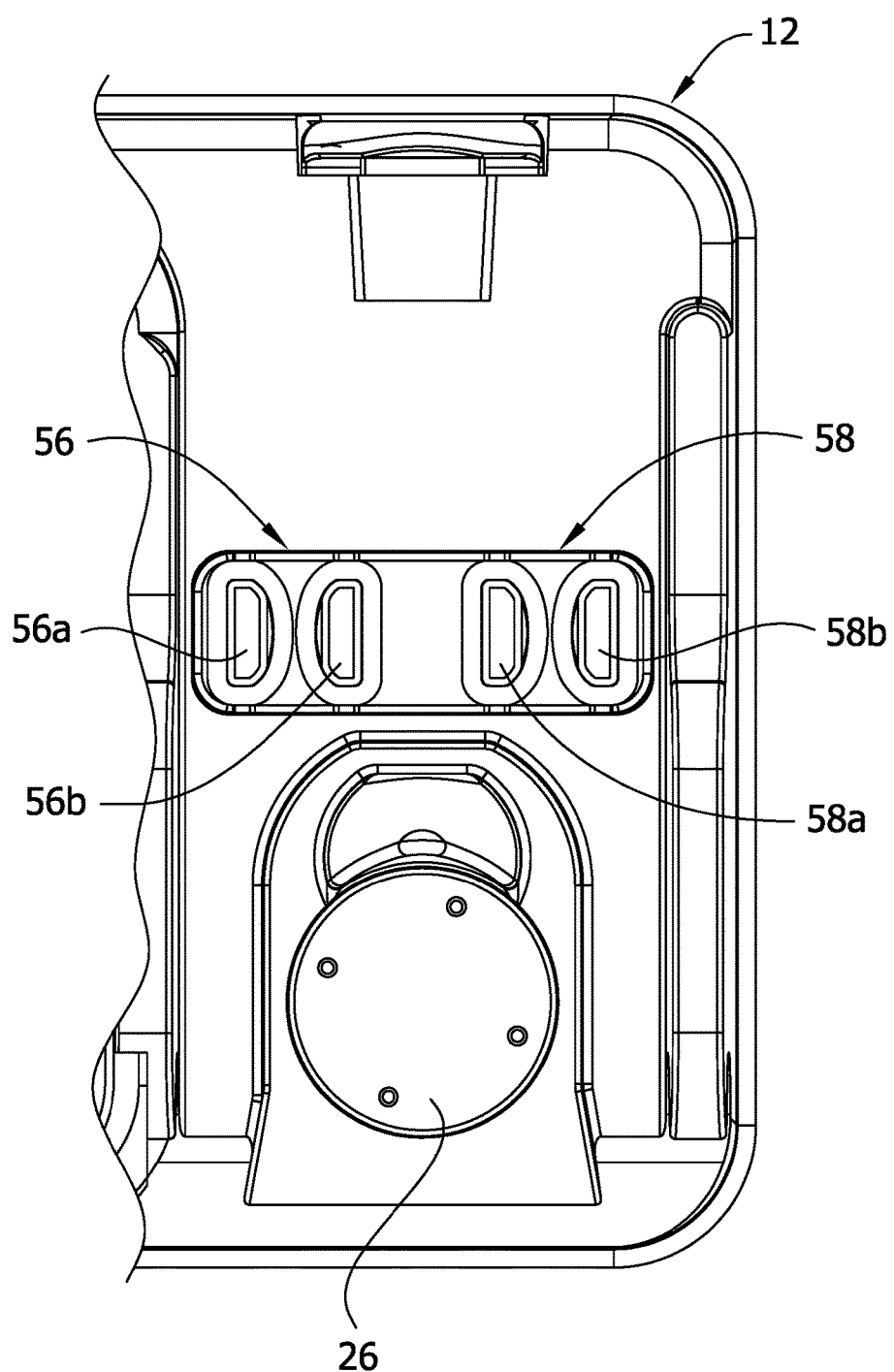
FIG. 3 is an enlarged, fragmentary front elevation of FIG. 2 with the feeding set removed from the enteral feeding pump.

Referring still to FIG. 4, the pump 10 includes a fluid monitoring system 62. The fluid monitoring system 62 may include the first and second fluid sensors 56, 58, respectively, the control unit 60 (e.g., a fluid monitoring controller of the control unit), a flow alarm 66, and a malfunction alarm 70. The control unit 60 is in communication with the first and second fluid sensors 56, 58, respectively, the flow alarm 66, and the malfunction alarm 70. Each of the flow and malfunction alarms 66, 70, respectively, may be audible, visual, vibratory or any combination thereof. In the illustrated embodiment, each of the first and second fluid sensors 56, 58, respectively, may include an ultrasonic generator 56a, 58a, respectively (broadly, a sensor signal generator), and an ultrasonic receiver 56b, 58b, respectively (broadly, a sensor signal receiver). For each sensor 56, 58, the ultrasonic generator 56a, 58a and the ultrasonic receiver 56b, 58b are on opposite sides of the cassette tube 46 such that the cassette tube is received between the generator and receiver (see FIG. 3). Each ultrasonic generator 56a, 58a (e.g., an ultrasonic transducer) is configured to receive a drive signal from the control unit 60 (more specifically, the processor 60a), and in response to the drive signal, generate an ultrasonic signal that is transmitted through the cassette tube 46 toward the corresponding ultrasonic receiver 56b, 58b. Each ultrasonic receiver 56b, 58b (e.g., an ultrasonic transducer) is configured to receive the ultrasonic signal and, in response to the received signal, generate an output signal. The control unit 60 (more specifically, the processor 60a) is configured to receive the output signal and determine and analyze a parameter value of the output signal, as described in more detail below.

Figure 5:
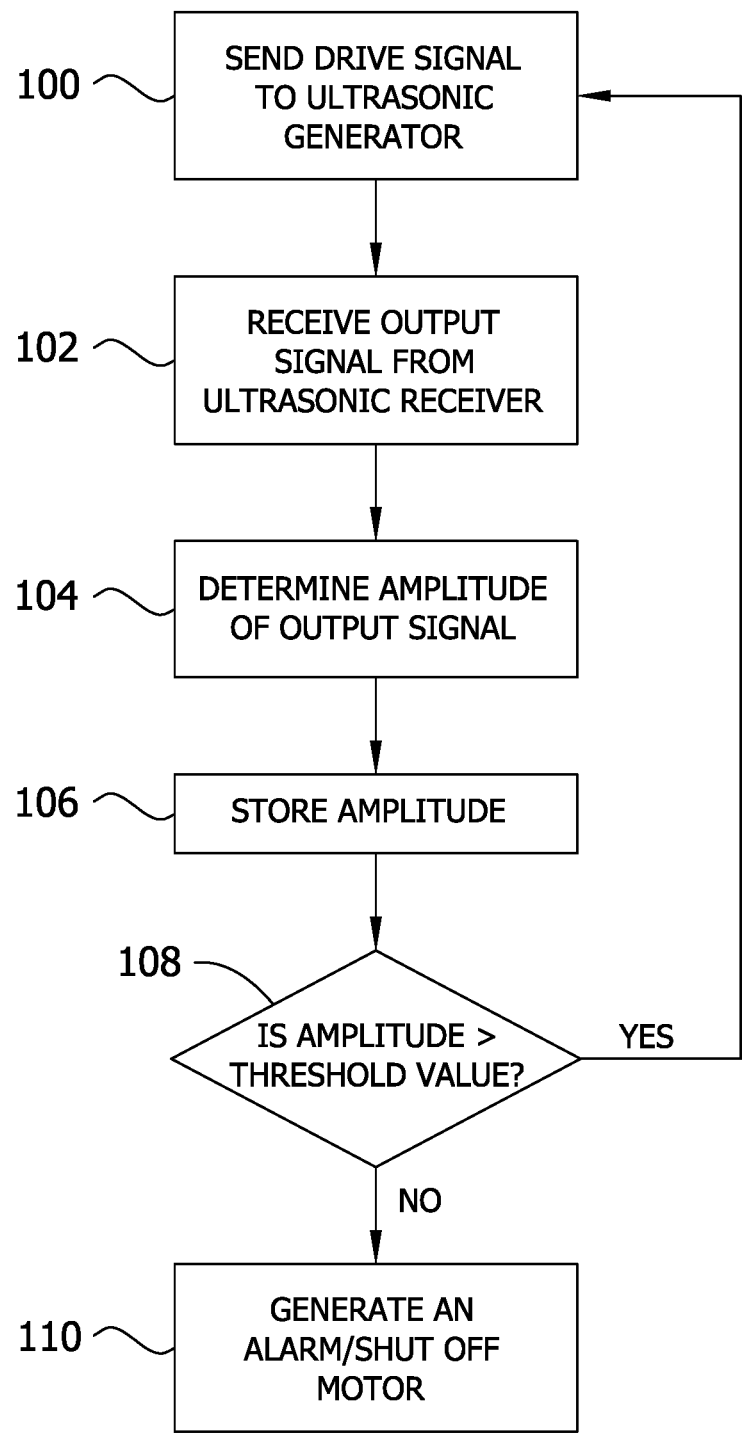
FIG. 5 is an exemplary flow chart illustrating a method performed in first mode of operation of a fluid monitoring system for monitoring a condition of fluid in the feeding set.

The fluid monitoring system 62 may include a first mode of operation (e.g., a fluid monitoring mode) for determining the condition of the fluid in the cassette tube 46, such as during operation of the pump 10 for delivering fluid to the patient. By determining the condition of the fluid in the cassette tube 46, the control unit 60 (e.g., the processor 60a) may be further configured to determine a condition of the feeding set 14 and the pump 10 in general. FIG. 5 illustrates instructions (e.g., software) stored in the computer readable storage medium (memory 60b) and executed by the processor 60a of the control unit 60 during the first mode of operation using the first fluid sensor 56. Similar, yet different, instructions may be stored for the second fluid sensor 58 or any additional fluid sensors. At 100, the control unit 60 (e.g., the processor 60a) generates a drive signal that is received by the ultrasonic generator 56a of the first fluid sensor 56. The drive signal may have a substantially constant frequency matching a resonant frequency of the ultrasonic generator 56a (e.g., between 1 to 3 MHz, and in one example about 2.25 MHz). In response to the drive signal, the ultrasonic generator 56a resonates, producing an ultrasonic signal that propagates through the cassette tube 46 and toward the ultrasonic receiver 56b. At 102, the control unit 60 (e.g., the processor 60a) receives the output signal from the ultrasonic receiver 56b of the first fluid sensor 56. At 104, the control unit 60 (e.g., the processor 60a) determines the amplitude of the output signal (broadly, a parameter value of the output signal). In other embodiments, other parameter values of the output signal (e.g., frequency, phase shift, etc.) may be determined and analyzed by the control unit 60 (e.g., the processor 60a) to determine the condition of the fluid in the cassette tube 46. At 106, the control unit 60 (e.g., the processor 60a) stores the amplitude of the output signal in the memory 60b. At 108, the control unit 60 (e.g., the processor 60a) compares the stored amplitude to a threshold value that is stored in computer readable storage medium. If the stored amplitude is above the threshold value, indicating that there is fluid in the cassette tube 46, the control unit 60 (e.g., the processor 60a) may return to step 100 after a predetermined amount of time and/or communicate to the user, such as by the user interface 16, that there is fluid in the feeding set 14. If the determined amplitude is not above (e.g., at or below) the threshold value, indicating that there is air in the cassette tube 46 and/or the tube is empty, then at 110 the control unit 60 (e.g., the processor 60a) activates the flow alarm 66 and/or shuts off the motor 52. It is understood that the fluid monitoring system 62 may include additional instructions and/or different instructions for monitoring a flow condition in the feeding set 14.

In another example, turning to the second fluid sensor 58, the control unit 60 (e.g., the processor 60a) may analyze the amplitude of the output signal to determine if the amplitude is above a threshold value stored in computer readable storage medium. This may indicate that the pressure in the cassette tube 46 is indicative of a downstream occlusion. The control unit 60 (e.g., the processor 60a) may activate the flow alarm 66 in response to the detection of an occlusion and/or shut off the motor 52.

The fluid monitoring system 62 may also include a second mode of operation (e.g., a malfunction detecting mode) for determining if the fluid monitoring system is malfunctioning. In one example, the control unit 60 may be configured (e.g., the processor 60a is programmed) to generate a second drive signal that is different from the first drive signal used in the first mode of operation. In response to the second drive signal, the ultrasonic generator 56a, 58a (broadly, the signal generator) generates an ultrasonic signal, different from the first ultrasonic signal, that is transmitted through the cassette tube 46 to the ultrasonic receiver 56b, 58b (broadly, the signal receiver). The ultrasonic receiver 56b, 58b generates an output signal in response to the transmitted signal. The control unit 60 (e.g., the processor 60a) receives the output signal from the ultrasonic receiver 56b, 58b, determines a parameter value(s) of the received output signal, and analyzes the parameter value(s) to determine if it corresponds with an anticipated or expected parameter value(s) associated with the second drive signal(s). In other words, in the second mode of operation, the fluid monitoring system 62 determines whether the ultrasonic receiver 56a, 58a is detecting an anticipated or expected ultrasonic signal in accordance with the second drive signal. If the ultrasonic receiver 56a, 58a is not detecting the anticipated or expected ultrasonic signal, then this indicates that the fluid monitoring system 62 is malfunctioning, and the control unit (e.g., the processor 60a) may activate the malfunction alarm 70 and/or shut off the motor 52.

In one embodiment of the second mode of operation, the control unit 60 (e.g., the processor) generates a second drive signal having a varying parameter (e.g., a varying frequency, such as when the first drive signal has a constant frequency). For example, where the fluid sensor 56, 58 includes an ultrasonic generator 56a, 58a, the control unit 60 (e.g., the processor 60a) may generate a sweep drive signal having a frequency (or other parameter) that varies over time. The sweep signal may have an initial frequency that is one of less than and greater than the frequency necessary for the ultrasonic generator 56a, 58a to produce the ultrasonic signal, and an ending frequency that is the other of greater than and less than the frequency necessary for the ultrasonic generator to produce the ultrasonic signal. The control unit 60 (e.g., the processor 60a) determines and stores amplitudes of the output signal generated by the ultrasonic receiver 56b, 58b. The stored amplitudes are analyzed by the control unit 60 (e.g., the processor 60a) to determine if the output signal had a sufficient change in amplitude that is generally commensurate with the change in frequency of the sweep signal. If the output signal did not have a sufficient change in amplitude that is generally commensurate with the change in frequency of the sweep signal, then this is indicative that the fluid monitoring system 62 is malfunctioning. In response, the control unit (e.g., the processor 60a) may activate the malfunction alarm 70 (FIG. 4).

Figure 6:
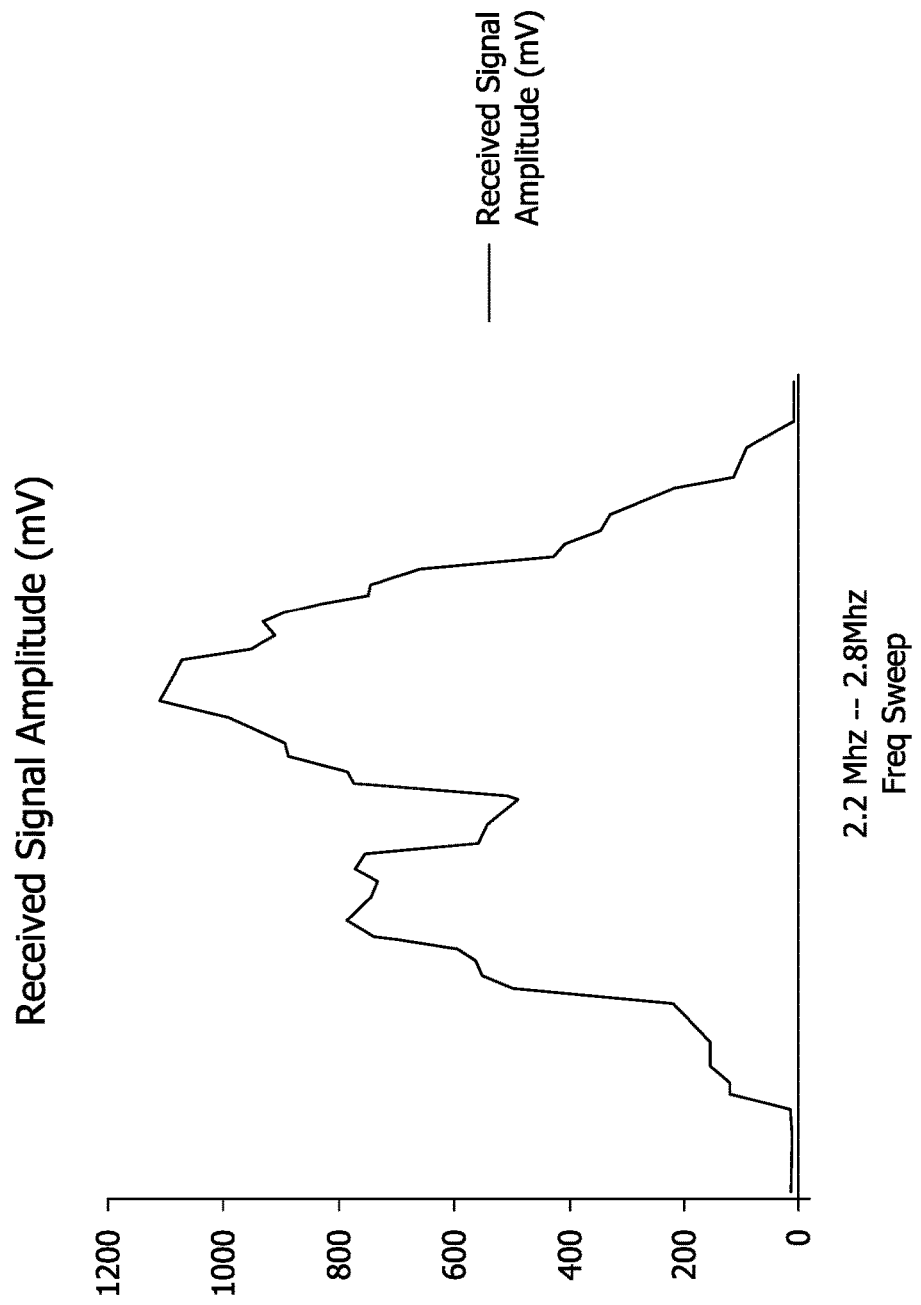
FIG. 6 is graph depicting the response of a non-malfunctioning fluid monitoring system during a second mode operation.
Figure 7:
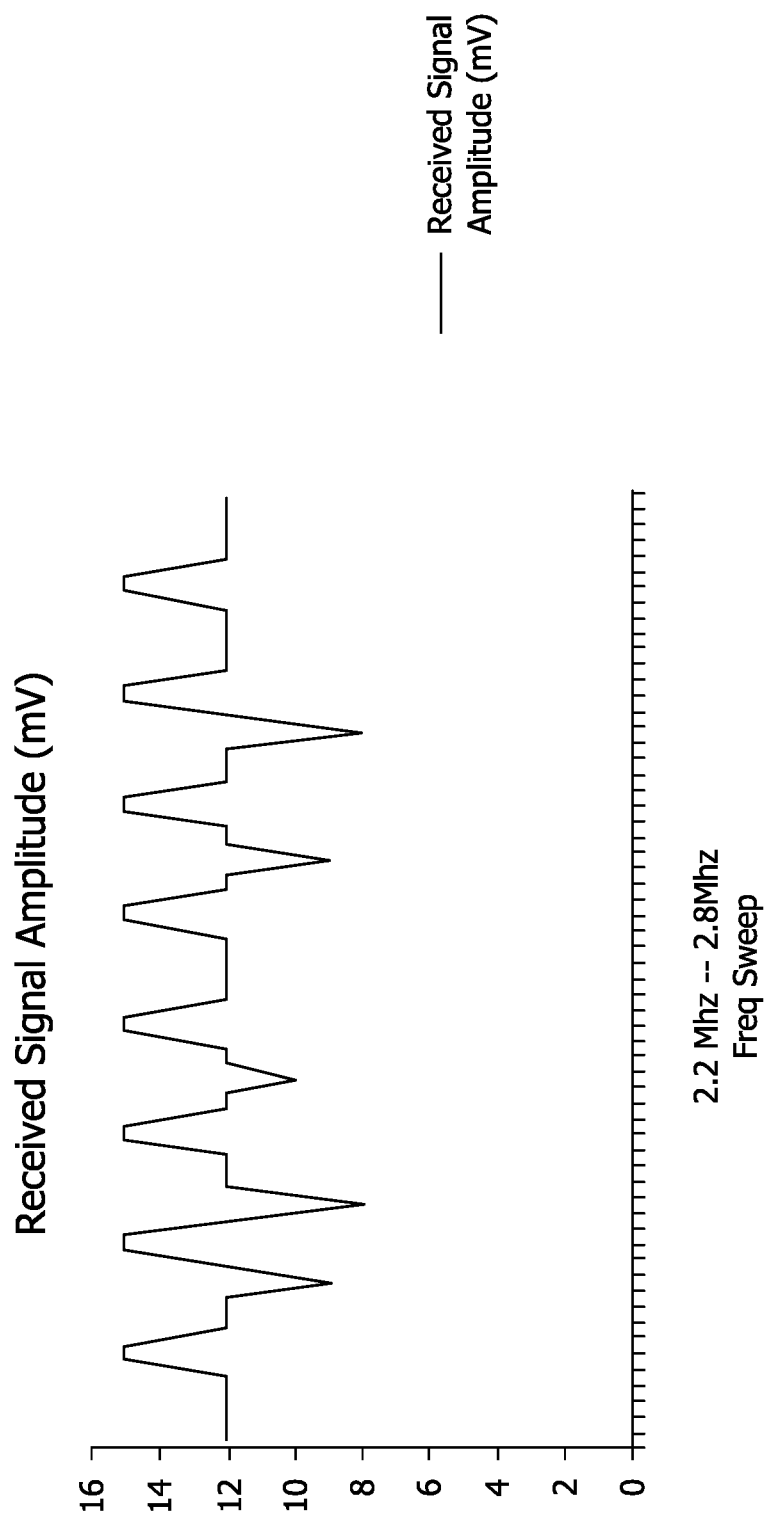
FIG. 7 is a graph depicting a low fail response of a malfunctioning fluid monitoring system during the second mode of operation.
Figure 8:
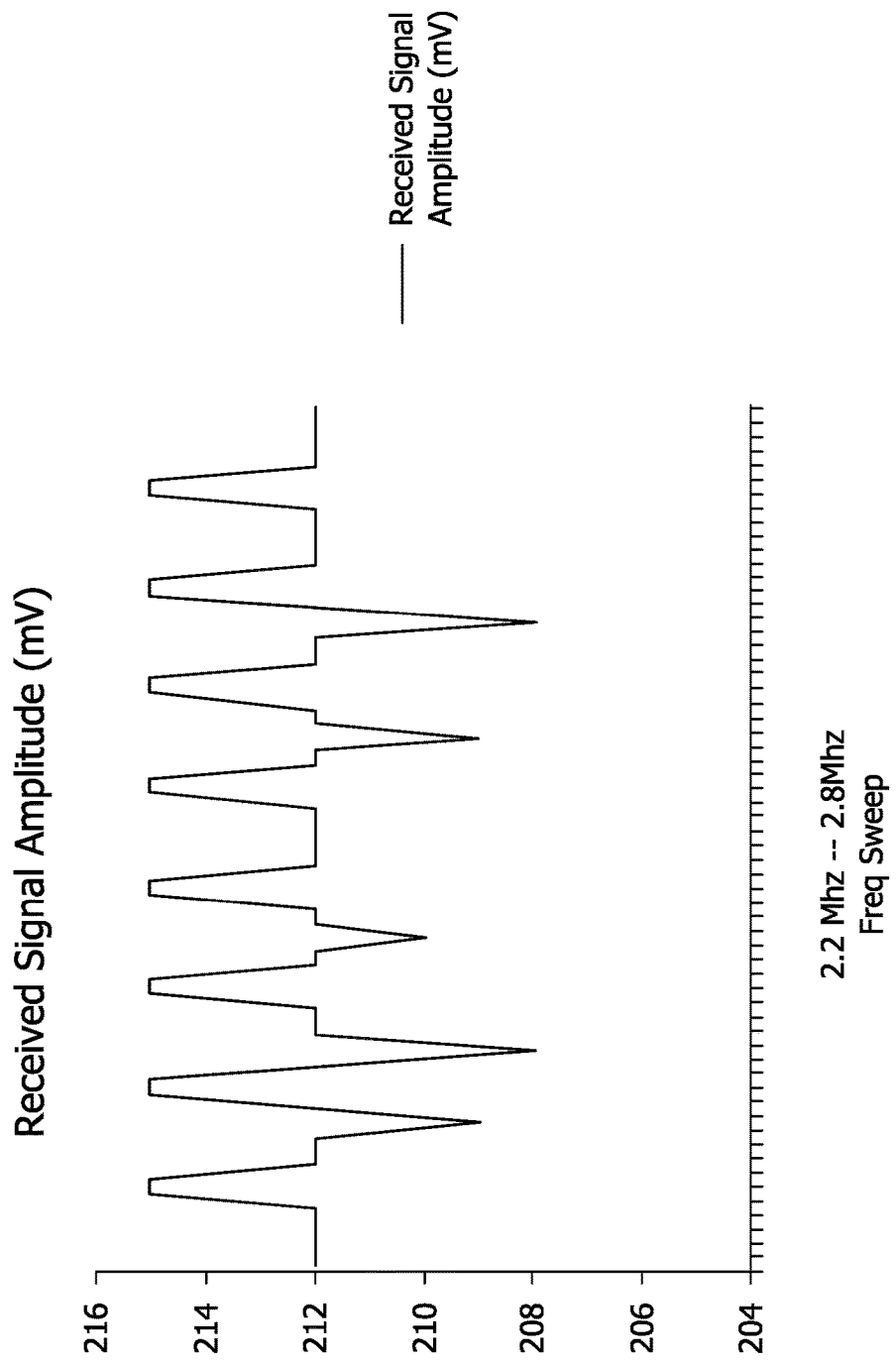
FIG. 8 is a graph depicting a high fail response of a malfunctioning fluid monitoring system during the second mode of operation.

As non-limiting illustrations, FIGS. 6-8 are graphs depicting the change in amplitude of the output signal in response to the frequency change of the sweep signal (from 2.2 MHz to 2.8 MHz) delivered to the first fluid sensors 56 of three different fluid monitoring systems 62. As can be observed from FIGS. 6-8, the change in amplitude of the output signal indicative of the sweep signal frequency change in a non-malfunctioning fluid monitoring system 62 (e.g., FIG. 6) is much greater than the change in amplitude of the output signal indicative of system noise in a malfunctioning fluid monitoring system 62 (e.g., FIGS. 7 and 8). FIG. 6 is a graph depicting the response of a non-malfunctioning fluid monitoring system 62 during the second mode operation. As can be observed from FIG. 6, there is detectable and constant change in amplitude of the output signal (from about 0 mV to about 1100 mV) as the frequency of the drive signal is swept. As illustrated, the amplitude of the output signal undergoes a corresponding change in response to every change in frequency of the swept drive signal. FIG. 7 is a graph depicting a low fail response of a malfunctioning fluid monitoring system 62 during the second mode of operation. As can be observed from FIG. 7, there is a relatively small change in amplitude of the output signal in a low range (from about 8 mV to about 15 mV) as the frequency of the drive signal is swept. This is an indication that the malfunction is related to the output signal (e.g., the ultrasonic receiver 56b is malfunctioning) or the malfunction is related to the input signal (e.g., the ultrasonic generator 56a is malfunctioning). Moreover, because the amplitude of the output signal is relatively small, during the first mode of operation the fluid monitoring system 62 may give an indication that there is no fluid in the tube, although this is not necessarily the case. FIG. 8 is a graph depicting a high fail response of a malfunctioning fluid monitoring system 62 during the second mode of operation. As can be observed from FIG. 8, there is a relatively small change in amplitude of the output signal (from about 208 mV to about 215 mV) as the frequency of the drive signal is swept. This is an indication that the malfunction is related to the output signal (e.g., the ultrasonic receiver 56b is malfunctioning) or the malfunction is related to the input signal (e.g., the ultrasonic generator 56a is malfunctioning). Moreover, because the amplitude of the output signal is relatively large, during the first mode of operation the fluid monitoring system 62 would give an indication that there is fluid in the cassette tube, although this is not necessarily the case.

Figure 9:
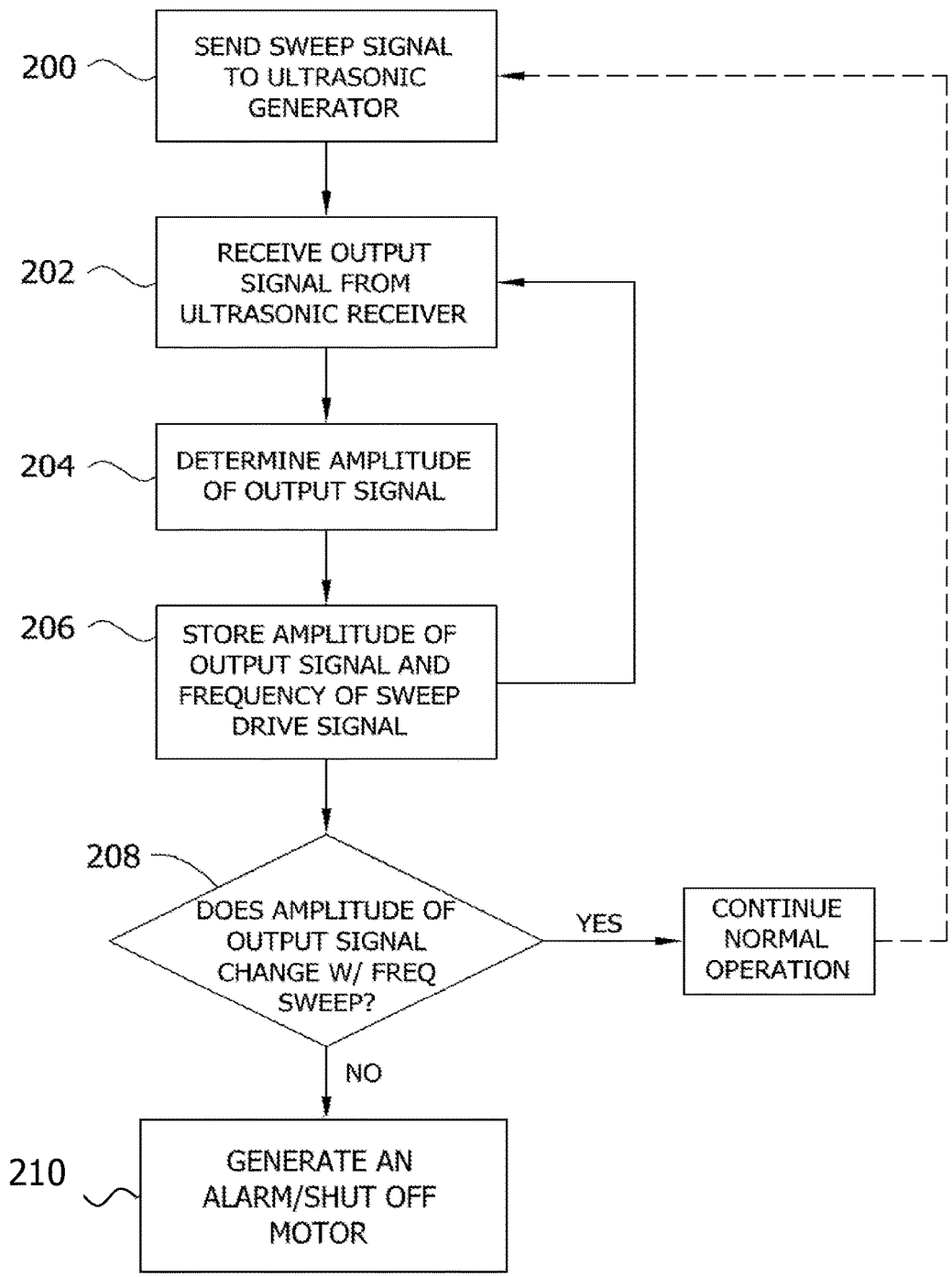
FIG. 9 is an exemplary flow chart illustrating a method performed in a second mode of operation of the fluid monitoring system for determining if the fluid monitoring system is malfunctioning.

One example of steps that may be performed by the control unit 60 (e.g., the processor 60a) in the second mode of operation to test the first fluid sensor 56 is depicted by a flow chart in FIG. 9. In particular, FIG. 9 illustrates instructions stored in the computer readable storage medium (memory 60b) of the control unit that are executed or run by the processor 60a. Similar, yet different, instructions may be stored to test the second fluid sensor 58 or any additional fluid sensors. The control unit 60 may perform the second mode of operation as the pump 10 is operating and on a periodic basis. At 200, the control unit 60 (e.g., the processor 60a) generates a sweep signal that is received by the ultrasonic generator 56a of the first sensor 56. The sweep signal may sweep through a range of drive frequencies. For example, the sweep signal may increase in frequency, at incremental steps, from an initial frequency that is lower than the frequency required to function the ultrasonic generator (e.g., 2.2 MHz) to an ending frequency that is higher than the frequency required to function the ultrasonic generator (e.g., 2.8 MHz). At 202, the control unit 60 (e.g., the processor 60a) receives the output signal from the ultrasonic receiver 56b of the first sensor 56. At 204, the control unit 60 (e.g., the processor 60a) determines the amplitude of the output signal (broadly, a parameter value of the output signal). In other embodiments, other parameter values of the output signal (e.g., frequency, phase shift, etc.) may be determined and analyzed by the control unit 60 (e.g., the processor 60a) to determine the condition of the fluid in the cassette tube 46. At 206, the control unit 60 (e.g., the processor 60a) stores the determined amplitude and the frequency of the sweep signal that produced the determined amplitude in the memory 60b. The control unit 60b repeats steps 202 to 206 until the sweep signal has ended. At 208, the control unit 60 (e.g., the processor 60a) determines if the amplitude of the output signal changes in accordance with the sweep signal. This step 208 may be accomplished by analyzing the stored amplitudes of the output signal to determine if there was a change in amplitude of the output signal over the frequency sweep. If the amplitude does not change in accordance with the sweep signal, then the control unit 60 (e.g., the processor 60a) may activate the malfunction alarm 70 at 210 indicating that the fluid monitoring system 62 is malfunctioning. The control unit 60 (e.g., the processor 60*a*) may also shut off the motor 52. If the amplitude does change in accordance with the sweep signal, then the control unit 60 (e.g., the processor 60*a*) continues with normal operation (e.g., normal pumping according to protocol) and stops the second mode of operation.

Embodiments can be implemented in digital electronic circuitry, or in computer hardware, firmware, software, or in combinations thereof. The controller of the compression system can be implemented in a computer program product tangibly embodied or stored in a machine-readable storage device for execution by a programmable processor; and method actions can be performed by a programmable processor executing a program of instructions to perform functions of the controller of the compression system by operating on input data and generating output. The controller of the compression system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits) or FPGAs (field programmable logic arrays).

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above constructions, products, and methods without departing from the scope of aspects of the invention, it is intended that all matter contained in the above description and shown in the accompanying drawings shall be interpreted as illustrative and not in a limiting sense.

The invention claimed is:

1. A flow control apparatus for use in delivering fluid to a patient comprising:
   a housing configured to receive a fluid delivery set having a fluid tube through which fluid is delivered to the patient; and
   a fluid monitoring system including:
      a fluid sensor including a signal generator configured to transmit a sensor signal through the fluid tube of the fluid delivery set, and a signal receiver configured to receive the sensor signal transmitted through the fluid tube and generate an output signal in response to the received sensor signal, and
      a control unit comprising a memory device, one or more processors, and computer executable instructions embodied on a computer readable storage medium,
   wherein the fluid monitoring system has a fluid monitoring mode during which the computer executable instructions cause the one or more processors to:
      send a first drive signal to the signal generator of the fluid sensor causing the signal generator to generate and transmit a first sensor signal through the fluid tube,
      receive a first output signal from the signal receiver of the fluid sensor, wherein the first output signal is generated by the fluid sensor in response to the received first sensor signal transmitted through the fluid tube, and
      determine a flow condition of any fluid in the fluid tube based on the output signal from the signal receiver, and
   wherein the fluid monitoring system has a malfunction detecting mode during which the computer executable instructions cause the one or more processors to:
      send a second drive signal, different from the first drive signal, to the signal generator causing the signal generator to generate and transmit a second sensor signal, different from the first sensor signal, through the fluid tube to the signal receiver of the sensor, said second drive signal having at least one parameter value that changes,
      receive a second output signal from the signal receiver of the fluid sensor, wherein the second output signal is generated by the signal receiver in response to receiving the second sensor signal transmitted through the fluid tube, said second output signal having at least one parameter value that changes, and
      detect at least one of a first malfunction of the fluid monitoring mode erroneously indicative of the fluid not being within the fluid tube and a second malfunction of the fluid monitoring mode erroneously indicative of the fluid being within the fluid tube when the change of the parameter value of the second output signal differs by a smaller amount relative to the change of the parameter value of the second drive signal.

2. The flow control apparatus of claim 1 wherein the instructions to detect the first malfunction and the second malfunction of the fluid monitoring mode include instructions to determine whether the parameter value of the second output signal changes by more than a predetermined amount in response to the second drive signal.

3. The flow control apparatus of claim 1 wherein the instructions to send the second drive signal include instructions to send a drive signal that sweeps over a range of drive signals from a frequency that is too low to generate an output signal from the signal receiver to a frequency higher than the signal receiver requires to generate an output signal.

4. The flow control apparatus of claim 3 wherein the parameter value of the second output signal comprises an amplitude value thereof.

5. The flow control apparatus of claim 4 wherein the instructions to detect the first malfunction of the fluid monitoring mode include instructions to determine when the amplitude value of the second output signal is relatively smaller during the change in the frequency of the drive signal that sweeps over the range of drive signals, and wherein the instructions to detect the second malfunction of the fluid monitoring mode include instructions to determine when the amplitude value of the second output signal is relatively larger during the change in the frequency of the drive signal that sweeps over the range of drive signals.

6. The flow control apparatus of claim 1, wherein the fluid monitoring system further includes a second fluid sensor including a second signal generator configured to transmit a second sensor signal through the fluid tube of the fluid delivery set, and a second signal receiver configured to receive the second sensor signal transmitted through the fluid tube and generate a third output signal in response to the received second sensor signal, and wherein the computer executable instructions cause the one or more processors to:
analyze an amplitude of the third output signal, and
detect an occlusion in the fluid tube when the amplitude of the third output signal is above a threshold value stored in the computer readable storage medium.

7. A computer-implemented method of monitoring fluid in a fluid tube of a flow control apparatus, the computer-implemented method comprising:

performing a fluid monitoring operation including:
sending a first drive signal to a signal generator of a fluid sensor causing the signal generator to generate and transmit a first sensor signal through the fluid tube to a signal receiver of the sensor,
receiving a first output signal from the signal receiver of the fluid sensor, wherein the first output signal is generated by the fluid sensor in response to the received first sensor signal transmitted through the fluid tube, and
determining a flow condition of any fluid in the fluid tube based on the first output signal from the signal receiver; and performing a malfunction detection operation including:
sending a second drive signal, different from the first drive signal, to the signal generator of the fluid sensor, wherein the second drive signal causes the signal generator to generate and transmit a second sensor signal, different from the first sensor signal, through the fluid tube to the signal receiver of the sensor, said second drive signal having at least one parameter value that constantly changes as a frequency of the second drive signal sweeps over a range of drive signals,
receiving a second output signal from the signal receiver of the fluid sensor, wherein the second output signal is generated by the signal receiver in response to receiving the second sensor signal transmitted through the fluid tube, said second output signal having at least one parameter value, and
detecting at least one of a first malfunctioning of the fluid monitoring system erroneously indicative of the fluid not being within the fluid tube and a second malfunctioning of the fluid monitoring system erroneously indicative of the fluid being within the fluid tube based on changes of the parameter value of the second output signal from the signal receiver being smaller relative to the changes of the parameter value of the second drive signal.

8. The computer implemented method of claim 7 wherein detecting the first malfunctioning and the second malfunctioning of the fluid monitoring system includes determining whether the parameter value of the second output signal changes by more than a predetermined amount in response to the second drive signal.

9. The computer implemented method of claim 7 wherein sending the second drive signal includes sending a drive signal that sweeps over a range of drive signals from a frequency that is too low to generate an output signal from the signal receiver to a frequency higher than the signal receiver requires to generate an output signal.

10. The computer implemented method of claim 9 wherein the parameter value of the second output signal comprises an amplitude value thereof, and wherein the parameter value of the second drive signal comprises an amplitude value thereof.

11. The computer implemented method of claim 10 wherein detecting the first malfunctioning of the fluid monitoring system includes determining when the amplitude value of the second output signal is smaller relative to the amplitude value of the second drive signal during the change in the frequency of the second drive signal that sweeps over the range of drive signals, and wherein detecting the second malfunctioning of the fluid monitoring system includes determining when the amplitude value of the second output signal is larger relative to the amplitude value of the second drive signal during the change in the frequency of the second drive signal that sweeps over the range of drive signals.

12. A flow control apparatus comprising a memory, one or more processors and computer executable instructions embodied on a computer readable storage medium, the computer executable instructions including instructions for causing the one or more processors to:

perform a fluid monitoring operation including:
sending a first drive signal to a signal generator of a fluid sensor causing the signal generator to generate and transmit a first sensor signal through the fluid tube to a signal receiver of the sensor,
receiving a first output signal from the signal receiver of the fluid sensor, wherein the first output signal is generated by the fluid sensor in response to the received first sensor signal transmitted through the fluid tube, and
determining a flow condition of any fluid in the fluid tube based on the first output signal from the signal receiver; and perform a malfunction detection operation including:
sending a second drive signal, different from the first drive signal, to the signal generator of the fluid sensor, wherein the second drive signal causes the signal generator to generate and transmit a second sensor signal, different from the first sensor signal, through the fluid tube to a signal receiver of the sensor, said second drive signal having at least one parameter value that changes during said sending, and said second drive signal sweeping over a range of drive signals from a frequency that is too low to generate an output signal from the signal receiver to a frequency higher than the signal receiver requires to generate an output signal,
receiving a second output signal from the signal receiver of the fluid sensor, wherein the second output signal is generated by the signal receiver in response to receiving the second sensor signal transmitted through the fluid tube, said second output signal having at least one parameter value, and
detecting at least one of a first malfunctioning of the fluid monitoring system erroneously indicative of the fluid not being within the fluid tube and a second malfunctioning of the fluid monitoring system erroneously indicative of the fluid being within the fluid tube based on changes of the parameter value of the second output signal from the signal receiver being smaller relative to the changes of the parameter value of the second drive signal as the frequency thereof sweeps over the range of drive signals.

13. The flow control apparatus of claim 12 wherein detecting the first malfunctioning and the second malfunctioning of the fluid monitoring system includes determining whether the parameter value of the second output signal changes by more than a predetermined amount in response to the second drive signal.

14. The flow control apparatus of claim 12 wherein the parameter value of the second output signal comprises an amplitude value thereof, and wherein the parameter value of the second drive signal comprises an amplitude value thereof.

15. The flow control apparatus of claim 14 wherein detecting the first malfunctioning of the fluid monitoring system includes determining when the amplitude value of the second output signal is smaller relative to the amplitude value of the second drive signal during the change in the frequency of the second drive signal that sweeps over the range of drive signals, and
wherein detecting the second malfunctioning of the fluid monitoring system includes determining when the amplitude value of the second output signal is larger relative to the amplitude value of the second drive signal during the change in frequency of the second drive signal that sweeps over the range of drive signals.

16. A system comprising:
means for performing a fluid monitoring operation including:
means for sending a first drive signal to a signal generator of a fluid sensor causing the signal generator to generate and transmit a first sensor signal through the fluid tube to a signal receiver of the sensor,
means for receiving a first output signal from the signal receiver of the fluid sensor, wherein the first output signal is generated by the fluid sensor in response to the received first sensor signal transmitted through the fluid tube, and
means for determining a flow condition of any fluid in the fluid tube based on the first output signal from the signal receiver; and
means for performing a malfunction detection operation including:
means for sending a second drive signal, different from the first drive signal, to the signal generator of the fluid sensor, wherein the second drive signal causes the signal generator to generate and transmit a second sensor signal, different from the first sensor signal, through the fluid tube to a signal receiver of the sensor, said second drive signal having at least one parameter value that changes over time during said sending thereof,
means for receiving a second output signal from the signal receiver of the fluid sensor, wherein the second output signal is generated by the signal receiver in response to receiving the second sensor signal transmitted through the fluid tube, said second output signal having at least one parameter value, and
means for detecting at least one of a first malfunctioning of the fluid monitoring system erroneously indicative of the fluid not being within the fluid tube and a second malfunctioning of the fluid monitoring system erroneously indicative of the fluid being within the fluid tube based on changes of the parameter value of the second output signal from the signal receiver being smaller relative to the changes of the parameter value of the second drive signal.

17. The system of claim 16 wherein the means for detecting includes means for determining whether the parameter value of the second output signal changes by more than a predetermined amount in response to the second drive signal.

18. The system of claim 16 wherein the means for sending the second drive signal includes means for sweeping the second drive signal over a range from a frequency that is too low to generate an output signal from the signal receiver to a frequency higher than the signal receiver requires to generate an output signal.

19. The system of claim 18 wherein the parameter value of the second drive signal comprises an amplitude value thereof, and wherein the parameter value of the second output signal comprises an amplitude value thereof.

20. The system of claim 19 wherein the means for detecting includes means for determining when the amplitude value of the second output signal is smaller relative to the amplitude value of the second drive signal during the change in the frequency of the second drive signal that sweeps over the range of drive signals, and
wherein the means for detecting the second malfunctioning of the fluid monitoring system includes means for determining when the amplitude value of the second output signal is larger relative to the amplitude value of the second drive signal during the change in the frequency of the second drive signal.

* * * * *